United States Patent [19]

Schaefer

[11] 4,399,074
[45] Aug. 16, 1983

[54] PREPARATION OF TERTIARY ALKYL ISOCYANATES

[75] Inventor: Frederic C. Schaefer, Darien, Conn.

[73] Assignee: American Cyanamid Company, Stamford, Conn.

[21] Appl. No.: 371,915

[22] Filed: Apr. 26, 1982

[51] Int. Cl.³ .......................................... C07C 118/00
[52] U.S. Cl. ................................................ 260/453 P
[58] Field of Search ..................................... 260/453 P

[56] References Cited

U.S. PATENT DOCUMENTS 4,130,577 12/1978 Nagato et al. ................... 260/453 P
4,224,238 9/1980 Nagato et al. ................... 260/453 P Primary Examiner—Dolph H. Torrence
Attorney, Agent, or Firm—Steven J. Hultquist

[57] ABSTRACT

A process for the production of tertiary alkyl isocyanates, such as tetramethylxylylene diisocyanates, is disclosed in which the corresponding tertiary alkyl halide is reacted with an alkali metal cyanate utilizing a zinc-pyridine complex as a catalyst which has been prereacted with the cyanate before reaction with the halide.

8 Claims, No Drawings

PREPARATION OF TERTIARY ALKYL ISOCYANATES

This invention relates to tertiary alkyl isocyanates and in particular provides a method for producing mono- and poly-isocyanates by reaction of the corresponding tertiary alkyl halides with alkali metal cyanates.

This invention has general applicability to the preparation of alkyl isocyanates in which the isocyanato group is attached to a tertiary carbon atom and in particular isocyanates in which the tertiary alkyl carbon atom is a substituent on an aromatic nucleus. The invention has particular applicability to the preparation of diisocyanates, such as tetramethylxylylene diisocyanates, and is illustrated in that context below, but is also applicable to the preparation of a variety of isocyanates such as tertiary butyl isocyanate, dipentene diisocyanate and tri-(isocyanatoisopropyl)benzenes.

This invention specifically relates to production of tertiary alkyl isocyanates by the reaction of the corresponding tertiary alkyl halide with an alkali metal cyanate, such as is described in U.S. Pat. Nos. 4,130,577 and 4,224,238. These patents describe the preparation of a wide variety of tertiary alkyl isocyanates by such reaction in an aprotic organic solvent and in the presence of a catalyst selected from the mineral acid salts and carboxylic acid salts of zinc, iron, antimony, tin and cobalt. The catalyst can also desirably include promoters, such as tertiary amines.

It has been recognized that the proportion of the catalyst promoter, in the case of pyridine, should be on the order of 2 moles per mole of catalyst metal salt, such as zinc chloride. This is presumably because the catalytic agent is a complex involving one mole of zinc salt and 2 moles of the promoter, pyridine. In accordance with the present invention it has been found that when using catalysts with promoters, such as a zinc salt with pyridine, the order of addition of the reactants is important. Greatly improved yields are obtained through reaction of the initial zinc-pyridine complex with the alkali metal cyanate prior to contact with the tertiary alkyl halide.

Thus in accordance with the present invention the complex between the zinc salt and pyridine is first prepared, generally in a 1:2 mole ratio of these components. Thereafter, the complex is reacted with the alkali metal cyanate at least in a quantity of 2 equivalents of cyanate for each atom of zinc present, thus forming a complex of zinc, pyridine and cyanate anion containing 2 moles of pyridine and 2 equivalents of cyanate anion per atom of zinc. Thereafter, the zinc-pyridine-cyanate complex is reacted with the tertiary alkyl halide to form the tertiary alkyl isocyanate.

It has also been found as described in co-pending application Ser. No. 371,913 filed Apr. 26, 1982, that the presence of water is desireable in promoting the catalyzed reaction between alkali metal cyanate and a tertiary alkyl halide. Desirably the amount of water should be on the order of 0.02% to 0.2% based on the weight of the entire reaction mixture including solvents.

Thus in accordance with this invention, as indicated above, the alkyl halide utilized can be any alkyl halide in which the halogen is bonded to a tertiary carbon atom. The reaction is generally selective, and the same or similar functional groups, such as halides, attached to secondary or primary carbon atoms are nonreactive under the conditions of the reaction. Poly tertiary alkyl halides can be reacted to produce the corresponding polyisocyanates.

The alkali metal cyanate can be any alkali metal cyanate, but preferably is sodium cyanate. The proportions of halide to cyanate are generally stoichiometric or with a slight excess of cyanate and range between ratios of 1:0.8 to about 1:4, preferably in the range of 1:1–1:2, of equivalents of halide to moles of cyanate.

The preparation of the catalyst with promoter, pre-reaction of alkali metal cyanate and final reaction with alkyl halide are all preferably carried out in an aprotic organic solvent for the organic components which is non-reactive with hydrogen halides and forms neither salts nor adducts with hydrogen halides. The solvents which can be used are those known in the art for this reaction. Particularly suitable are halogenated aliphatic and aromatic hydrocarbons, methylene dichloride being preferred.

Generally the reaction of cyanate with alkyl halide is carried out between 0° C. and 100° C. for a sufficient period of time to convert the tertiary alkyl halide substantially to the corresponding tertiary alkyl isocyanate. In some circumstances higher temperatures may be used. Tertiary halides are usually unstable over 50° C., however and dehydrochlorination can occur at higher temperatures. The solvent can also limit the temperature. Methylene dichloride, for example, boils at 40° C. Normally the reactions are carried out at atmospheric pressure.

The preparation of the catalyst with promoter and pre-reaction with alkali metal cyanate take place readily at ambient, room temperatures, but higher and lower temperatures may be used.

Generally catalysts effective to promote the reaction of a tertiary alkyl halide with an alkali metal cyanate in accordance with this invention are zinc salts of mineral acids and various carboxylic acids. Zinc chloride has been found particularly effective. As is known in the art, only small amounts of catalyst are required, and preferably the amount is just that sufficient to obtain the desired reaction. Usually 0.5 to about 50 mole percent of catalyst, and preferably about 1 to 10 mole percent of catalyst, based on the starting tertiary alkyl halide, is utilized.

As noted, in accordance with this invention the catalyst is employed in conjunction with a promoter such as pyridine. The amount of pyridine is based on the amount of catalyst employed and preferably is 2.0 moles per mole of zinc salt. Preferably zinc chloride is employed as catalyst, and the zinc chloride and pyridine are first complexed and then reacted with the alkali metal cyanate. While two equivalents of cyanate are required to form the zinc-pyridine-cyanate complex, usually the cyanate requirements for reaction with the alkyl halide will dictate a substantial excess of cyanate over that required by the stoichiometry of the zinc-pyridine-cyanate complex.

In carrying out the reaction of a tertiary alkyl halide with an alkali metal cyanate in a solvent to produce the corresponding tertiary alkyl isocyanate utilizing as a catalyst a material, such as zinc chloride, promoted with a material, such as pyridine, the reaction is slow and the yields are poor. To illustrate a reaction mixture of 198 g of p-tetramethylxylylene dichloride, 226 g of sodium cyanate (90% pure, 0.5% $H_2O$) 5.36 g of zinc chloride and 6.1 g of pyridine in 575 g of methylene dichloride was stirred at 20°–25° C. for many hours.

After 3 hours an additional 5.4 g of zinc chloride was added. The reaction process was followed by gas-liquid chromatography with the results indicated in Table 1.

TABLE 1

| Time, Hrs. | Organic Product Distribution, Area % | | |
|---|---|---|---|
| | p-DIPEB | p-TMI | p-TMXDI |
| 2 | 43.5 | 41.2 | 13.6 |
| 3 | 39.7 | 43.2 | 16.7 |
| 4 | 36.5 | 45.5 | 16.9 |
| 20 | 25.2 | 43.5 | 24.2 | p-DIPEB = para-diisopropenylbenzene-the reactant tetramethylxylylene dichloride (p-TMXDC) is observed on GLC as the diene as a result of thermal dehydrochlorination during measurement. Part of the observed p-DIPEB may be real, as a result of dehydrochlorination in the reaction mixture.

p-TMI = the corresponding monoisocyanate which may be present in the reaction mixture both as p-chloroisopropyl-α,α-dimethylbenzyl isocyanate and as p-isopropenyl α,αdimethyl benzylisocyanate.

p-TMXDI = para-tetramethylxylylene diisocyanate.

It is believed the poor yields obtained when the catalyst and reactants are mixed together occurs because the solid zinc chloride reactant does not dissolve with sufficient rapidity to interact with the pyridine "promoter". Consequently the pyridine reacts with the alkyl halide to form the corresponding olefin and pyridine hydrochloride.

In small scale experiments utilizing the same ingredients with equipment provided with magnetic stirrers effective closer to the bottom of the reaction vessel the heavy zinc chloride crystals were better dispersed and reaction was much improved. It has nevertheless been found that the formation of the zinc-pyridine-cyanate complex prior to addition of the alkyl halide provides superior results as shown in the following series of small scale runs set forth in Table II.

In the experiment shown in Table II the following components were utilized:

20 g—p-TMXDC (0.087 mole)
22.4 g—NaOCN (90% pure; 0.31 mole)
0.54 g—ZnCl$_2$ (0.0040 mole)
0.61 g—pyridine (0.0077 mole)
58 ml CH$_2$Cl$_2$ Table II further sets forth the procedure and order of addition utilized. The symbology is the same as in Table I.

TABLE II

| Experiment No. | Procedure (at 25° C.) | Time, Hrs. | Reaction Progress (Area %, by GLC Analysis) | | |
|---|---|---|---|---|---|
| | | | p-DIPEB | p-DIPEB TMI | p-TMXDI |
| A | (a) Added ZnCl$_2$ to CH$_2$Cl$_2$ and stirred 15 min. | 2.5 | 7.8 | 23.3 | 64.1 |
| | (b) Added TMXDC, stirred 10 min. | 4 | 4.8 | 20.7 | 69.1 |
| | (c) Added Pyridine, stirred 10 min. | | | | |
| | (d) Added NaOCN, stirred | | | | |
| B | (a) and (b) as in Ex. No. A | 2 | No Apparent Reaction | | |
| | (c) no pyridine added | | | | |
| | (d) as in Ex. No. A | | | | |
| C | Repeat Ex. No. A | 2.5 | 9.7 | 25.4 | 61.8 |
| D | (a) Added TMXDC and NaOCN to CH$_2$Cl$_2$ | 4.25 | 2.0 | 16.4 | 74.5 |
| | (b) Added ZnCl$_2$, stirred 10 min. | 2.5 | 10.5 | 24.0 | 62.7 |
| | | 4.5 | 9.0 | 24.1 | 62.2 |
| | (c) Added Pyridine dropwise with stirring, continued stirring | | | | |
| E | (a) Added ZnCl$_2$ and Pyridine to CH$_2$Cl$_2$, stirred 15 min. | 2.5 | 2.1 | 15.8 | 76.0 |
| | (b) Added NaOCN, stirred 10 min. | 4.5 | 0.7 | 9.5 | 82.9 |
| | (c) Added TMXDC, stirred | | | | |

In Experiments A and C, above, the zinc chloridepyridine complex was allowed to interact directly with the p-TMXDC before introduction of the cyanate salt and dehydrochlorination occurred. It is believed the zinc was partially deactivated by crystallization of the difficultly soluble salt, pyridinium tetrachlorozincate. In the absence of pyridine, however, as shown in Experiment B, no reaction takes place whatsoever. Experiment D shows that addition of the sodium cyanate at the same time as the halide does not alleviate the problem even though contact of these precedes the addition of pyridine.

It has been found in accordance with the present invention with the addition of the halides being deferred until after the zinc chloride has been solubilized by its reaction with pyridine substantially greater yields are obtained. It has been found that yields are further improved by allowing time for the initially solubilized complex of zinc salt and pyridine to react with the cyanate anion and form the zinc-pyridine complex having two equivalents of cyanate anion and two moles of pyridine for each atom of zinc. Conversion of the zinc-pyridine complex in solvent mediums such as methylene dichloride with added alkyl metal cyanate, such as sodium cyanate, takes place in a short time, i.e., in 10 minutes as is shown in Experiment E.

The benefits of this procedure can be illustrated in an experiment in which 0.22 mole of sodium cyanate and 0.10 mole of p-TMXDC were added simultaneously to a solution of 0.0067 mole Zn(pyr)$_2$Cl$_2$ dissolved in 35 ml of methylene dichloride. The reaction was followed at 25° by GLC. Conversion to p-TMXDI was only 28% in 2 hours. When the sodium cyanate was added first and stirred with the zinc chloride-pyridine complex solution for at least 10 minutes before the dichloride was added a 48% conversion to p-TMXDI was obtained in 2 hours.

The following Examples further illustrate the preparation of tertiary alkyl isocyanates in accordance with this invention.

EXAMPLE 1

α,α-Dimethyl-4-Isopropenylbenzyl Isocyanate (p-TMI)

1067 g (6.7 mole) of p-diisopropenyl benzene was dissolved in three liters of methylene dichloride and treated at 0° C. with 6.7 moles of dry, gaseous hydrogen chloride. The resulting crude solution contained α,α-dimethyl-4-isopropenylbenzyl chloride as a predominant organic product.

A catalyst solution was prepared by stirring a mixture of 64.4 g zinc chloride, 75 g of pyridine and 1580 ml of methylene dichloride (0.002% $H_2O$) until an essentially clear solution was obtained (30 minutes). An additional 1800 ml of methylene dichloride and 1065 g (14.7 moles) of 90% sodium cyanate (0.5% $H_2O$) were then added, and the suspension was stirred for 15 minutes.

The chloride reagent solution prepared above was then gradually added over 10 minutes to the catalyst solution, and the reaction mixture was held at 20°–25° with gentle cooling.

After a 2 hour reaction period no further change was found to be occurring as determined by gas chromatography, and the reaction products, so determined were present in molar ratios of approximately 17:74:3 of diisopropenyl benzene: p-TMI;p-TMXDI.

The solvent was then distilled from the reaction mixture, and the residue was extracted with 3 liters of hexane. This extract was concentrated to recover 1448 g of crude p-TMI containing 4.06 mole (60.6% yield) of p-TMI. The crude p-TMI was then purified by flash distillation through a wiped film evaporator to remove polymeric by-products and residual zinc catalyst, and thereafter was fractionally distilled through a packed column; B.P. 121° C. at 5 mm Hg.

EXAMPLE 2

α,α-Dimethyl-3-Isopropenylbenzene Isocyanate m-TMI

This compound was prepared in the same manner as described with reference to p-TMI in Example 1 above, starting with 1,3-diisopropenylbenzene. Comparable yields were obtained; B.P. 118° C. at 5 mm Hg.

EXAMPLE 3

1,3,5-Tris(1-Isocyanato-1-Methylethyl) Benzene

A catalyst solution was prepared by stirring a mixture of zinc chloride (1.0 moles), pyridine (2.0 mole) and methylene dichloride until the solid dissolved. 1.42 moles of 90% sodium cyanate containing 0.5% $H_2O$ were added to 100 ml. of the solution so prepared which contained the equivalent of 24 m.moles of $Zn(pyr)_2Cl_2$. The mixture was stirred for an hour, and thereafter 0.33 moles of 1,3,5-tris(1-chloro-1-methylethyl)benzene dissolved in 530 methylene chloride was added.

After stirring overnight at room temperature gas chromatographic analysis indicated 81% conversion to triisocyanate had been achieved. The solvent was evaporated, and the product was recrystallized from hexane giving a 59% yield; M.P. 65.5–66.5° C.

EXAMPLE 4

2,6-Bis(1-Isocyanato-1-Methylethyl)Naphthalene 2,6-Bis(-1chloro-1-methylethyl)naphthalene (0.178 mole) was prepared by passing a stream of dry gasous hydrogen chloride through a methylene dichloride suspension of 2, 6-diisopropenylnaphthalene (37.2 g, 0.18 mole) which had previously been cooled to 4° C. After conversion of the diisopropenylnaphthalene to the dichloride the solvent was removed in vacuo at 30° C. leaving an off-white solid. The solid was redissolved in 250 ml. of methylene dichloride, cooled to 4° C. and slowly added to a cooled (4° C.) methylene dichloride suspension of sodium cyanate/zinc chloride catalyst solution. The catalyst solution had previously been prepared by vigorously stirring a suspension of zinc chloride (2.0 g,0.014 mole), pyridine (2.46 g, 0.03 mole), anhydrous, 90% sodium cyanate (34 g 0.47 mole) and 0.25 ml of water in 300 ml methylene dichloride for 2 hours at ambient temperature.

The reaction mixture was allowed to stand at 4° C. for two hours and then was allowed to warm to ambient temperature and stirred an additional 18 hours. Magnesium sulfate and Hyflo (a proprietary filtration aid) were then added. After 5 minutes the solution was filtered to remove solids. The solvent was then removed in vacuo leaving 57 g of an oily solid. The oily solid was mixed with 600 ml. of hexane, heated at 70° C. for one hour, filtered through Hyflo and then cooled to ambient temperature. The solid which crystallized was collected and air dried, affording 25 g (first crop) of product. The mother liquor was then concentrated and cooled affording a second crop of 12 g. The final product, 37 g (70% yield), was found to have a chloride level of 370 ppm and an isocyanate content equivalent to 6.66 meq/g. (melting range 85.5°–87° C.)

EXAMPLE 5

α,α-Dimethylbenzylisocyanate

α,α-Dimethylbenzylchloride was prepared by passing a stream of dry hydrogen chloride gas through a solution of methylene dichloride (750 ml.) and α-methylstyrene (500 g, 4.2 moles) at 4° C. The reaction and work-up were employed for the paration of 2,6-bis(1-isocyanato-1-methylethyl)naphthalene described in Example 4. The resulting monochloride was dissolved in 750 ml. methylene dichloride and was added to a cooled (4° C.) catalyst solution previously prepared from anhydrous, 90% sodium cyanate (389 g,5.39 moles), pyridine (50 ml., 0.633 mole), zinc chloride (39.15 g,0.28 mole) and 1 ml. $H_2O$ in 1075 ml methylene dichloride.

After the reaction mixture had been stirred at ambient temperature for 3 days magnesium sulfate and Hyflo were added and the solution filtered to remove solids. Solvent was then removed in vacuo leaving an oil which was found to be 66% dimethyl benzylisocyanate and 33% α-methylstyrene. The isocyanate was further purfied by fractional distillation affording 275 g (45%) of α,α-dimethylbenzylisocyanate.

I claim:

1. A process for production of a tertiary alkyl isocyanate from the corresponding tertiary alkyl halide which comprises:

a. preparing a complex of a zinc salt of an acid selected from mineral acids and carboxylic acids and pyridine in a 1:2 mole ratio, b. thereafter reacting said zinc-pyridine complex with an alkali metal cyanate to form a zinc-pyridine-cyanate complex containing 2 equivalents of cyanate anion per atom of zinc, and c. reacting said zinc-pyridine-cyanate complex with said tertiary alkyl halide in an aprotic solvent at a temperature of from 0° C. to 100° C. to form said tertiary alkyl isocyanate.

2. A process according to claim 1 in which said zinc salt is zinc chloride.

3. A process according to claim 2 in which said solvent is methylene dichloride.

4. A process according to claim 2 in which said halide is a di(2-chloroisopropyl)benzene dichloride.

5. A process according to claim 2 in which said halide is an α,α-dimethyl-isopropenyl benzyl chloride.

6. A process according to claim 2 in which said halide is a tris(2-chloroisopropyl)benzene.

7. A process according to claim 2 in which said halide is a di(2-chlorisopropyl)naphthalene.

8. A process according to claim 2 in which said halide is α,α-dimethylbenzyl chloride.

* * * * *